(12) United States Patent
Stumpf et al.

(10) Patent No.: US 12,064,499 B2
(45) Date of Patent: Aug. 20, 2024

(54) LIQUID FRAGRANCE COMPOSITIONS

(71) Applicant: International Flavors & Fragrances Inc., Union Beach, NJ (US)

(72) Inventors: Craig Michael Stumpf, Union Beach, NJ (US); Jason Leslie Geno, Union Beach, NJ (US); Joseph Brain, Union Beach, NJ (US); Timothy Young, Union Beach, NJ (US); Nathan Wakelin, Hilversum (NL)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 815 days.

(21) Appl. No.: 17/261,624

(22) PCT Filed: Jul. 25, 2019

(86) PCT No.: PCT/US2019/043336
§ 371 (c)(1),
(2) Date: Jan. 20, 2021

(87) PCT Pub. No.: WO2020/023690
PCT Pub. Date: Jan. 30, 2020

(65) Prior Publication Data
US 2021/0269739 A1    Sep. 2, 2021

Related U.S. Application Data

(60) Provisional application No. 62/703,214, filed on Jul. 25, 2018.

(51) Int. Cl.
*A61K 8/06* (2006.01)
*A61G 13/00* (2006.01)
*A61K 8/37* (2006.01)
*A61Q 13/00* (2006.01)

(52) U.S. Cl.
CPC .............. *A61K 8/062* (2013.01); *A61G 13/00* (2013.01); *A61K 8/375* (2013.01)

(58) Field of Classification Search
CPC ...... A61K 8/062; A61K 8/8152; A61K 8/375; A61Q 13/00; A61L 9/012
USPC ........................................................ 512/2, 1
See application file for complete search history.

(56) References Cited

U.S. PATENT DOCUMENTS

| | | |
|---|---|---|
| 2004/0102358 A1 | 5/2004 | Scivoletto |
| 2012/0097754 A1 | 4/2012 | Vlad |
| 2015/0118169 A1* | 4/2015 | Hakozaki ............... A61K 8/361 424/62 |
| 2015/0231058 A1 | 8/2015 | Heisler |

FOREIGN PATENT DOCUMENTS

| | | |
|---|---|---|
| CN | 108815054 | * 11/2018 |
| WO | 2018067984 A1 | 4/2018 |

OTHER PUBLICATIONS

Deng et al, CN 108815054 Machine Translation, Nov. 16, 20118 (Year: 2018).*
International Preliminary Report on Patentability in PCT/US2019/043336 dated Jan. 26, 2021.
International Search Report and Written Opinion in PCT/US2019/043336 dated Nov. 11, 2019.

* cited by examiner

*Primary Examiner* — Jessica Whiteley

(57) ABSTRACT

A liquid fragrance composition contains (i) 3 wt % to 40 wt % of a fragrance, (ii) 0.5 wt % to 5 wt % of glyceryl ricinoleate, and (iii) 60 wt % to 95 wt % of water. Also disclosed are consumer products containing such a liquid fragrance composition.

17 Claims, No Drawings

LIQUID FRAGRANCE COMPOSITIONS

CROSS-REFERENCE TO RELATED APPLICATIONS

This application is the national phase under 35 U.S.C. § 371 of PCT International Application No. PCT/US2019/043336, filed Jul. 25, 2019, which claims priority to US patent application, Ser. No. 62/703,214, filed Jul. 25, 2018, the contents of which is are incorporated herein by reference in its entirety their entireties.

BACKGROUND

More and more consumers prefer a strong and long-lasting scent on consumer products such as household products, personal care products and fabric care products.

Traditionally, a fragrance is added to a consumer product base with a high level of a surfactant or ethanol. The fragrance is emulsified or solubilized as oil droplets that stabilized by the surfactant. The level of fragrance is limited due to the stability of the fragrance emulsion or solubility in the medium (hydro or hydro-alcoholic). Take conventional air freshening products for example. Some products contain excessive amount of solubilizing agents or co-solvents. See US20120097754. Other products utilize porous particles to entrap fragrances, leaving a large amount of solid waste after use. See US20030024997.

Oil-in-water emulsions have been used to incorporate fragrances in consumer products. However, such products conventionally contain a high level of surfactants to help solubilize the fragrance, which is relatively low, such as 6%. See U.S. Pat. Nos. 5,047,234 and 7,511,002.

There is a need to develop a liquid fragrance composition with a high dosage of fragrance and a low amount of surfactant.

SUMMARY OF THE INVENTION

This application is based on the unexpected discovery of a high performing liquid fragrance composition suitable for consumer products.

Accordingly, one aspect of this invention relates to liquid fragrance compositions each comprising: (i) 3 wt % to 40 wt % (e.g., 5 wt % to 35 wt %, preferably 8 wt % to 30 wt %, and more preferably 10 wt % to 3 wt %) of a fragrance, (ii) 0.5 wt % to 5 wt % (preferably 0.2 wt % to 3 wt %, and more preferably 0.5 wt % to 2.5 wt %) of glyceryl ricinoleate, and (iii) 60 wt % to 95 wt % of water. All amounts are based on the weight of the liquid fragrance composition.

In some embodiments, the liquid fragrance compositions are stable for at least 8 weeks (preferably at least 26 weeks) at a temperature of 25° C.

In some embodiments, the weight ratio of the fragrance to glyceryl ricinoleate is from 1:1 to 28:1 (preferably 2:1 to 28:1, more preferably 5:1 to 28:1, and most preferably 5:1 to 20:1).

Any of the above liquid fragrance compositions can further contain 0.3 wt % to 2 wt % of a thickening agent, such as an acrylate/$C_{10-30}$ alkyl acrylate crosspolymer.

The liquid fragrance compositions of this invention typically have a viscosity of 400 cP to 3000 cP (e.g., 800 cP to 3000 cP).

Any of the above liquid fragrance compositions preferably has a pH of 3.5 to 8 (more preferably 4 to 5 and 5.5 to 6.5).

In any liquid fragrance composition of this invention, the fragrance preferably contains the following components: (i) 0 wt % to 10 wt % of one or more Type (I) fragrance ingredients having a ClogP of less than 2, (ii) 80 wt % to 100 wt % of one or more Type (II) fragrance ingredients having a ClogP of 2 to 5, and (iii) 0 wt % to 20 wt % of one or more Type (III) fragrance ingredients having a ClogP of greater than 5. In a preferred embodiment, the fragrance contains 10 wt % or less of one or more Type (IV) fragrance ingredients having a primary hydroxyl group.

In some embodiments, the liquid fragrance composition is an oil-in-water emulsion, in which a plurality of fragrance oil droplets are dispersed in water, and the fragrance oil droplets each have a size of 0.1 μm to 200 μm (e.g., 0.5 μm to 150 μm and 5 μm to 75 μm) in diameter.

In other embodiments, the liquid fragrance compositions of this invention comprise a plurality of microcapsules, wherein each of the microcapsules contains a microcapsule core and a microcapsule wall encapsulating the microcapsule core.

Another aspect of this invention relates to a consumer product containing on any of the liquid fragrance compositions described above. The consumer product can be an air freshener, an air spray, a concentrated floor cleaner, or a laundry scent booster. Examples include a shampoo, a hair conditioner, a body lotion, a fine fragrance, a facial lotion, a facial tissue, a cleansing wipe, a hand soap, and an alcohol free perfume.

The details of one or more embodiments of the invention are set forth in the description below. Other features, objects, and advantages of the invention will be apparent from the description and from the claims.

DETAILED DESCRIPTION OF THE INVENTION

It has been found that certain liquid fragrance compositions unexpectedly provide a long-lasting, enhanced scent level in consumer applications while remaining stable with a high dosage of fragrance and a relatively low amount of a surfactant.

The liquid fragrance compositions of this invention are considered stable when, after a period of time (e.g., 4 weeks or 8 weeks), they has minimal or no separation and/or do not cream, foam or gel. For the purposes of the present invention, a stable liquid fragrance composition is one with less than 10%, less than 5% or less than 1% separation as determined by measuring the volume of the fragrance oil accumulated on the top or bottom of the fragrance composition as compared to total volume of the fragrance oil contained in the composition.

Each liquid fragrance composition is an oil-in-water emulsion with fragrance oil droplets dispersed homogeneously in a water phase. The oil droplets each have a size in diameter of 0.1 μm to 200 μm, preferably 0.5 μm to 150 μm, and more preferably 5 μm to 75 μm.

In some embodiments, the liquid fragrance composition is transparent or opaque.

Viscosity

Preferably, the viscosity of the liquid fragrance compositions can be readily measured with a viscometer, such as Brookfield DV-111 Ultra Programmable viscometer (Brookfield Engineering Laboratories, Inc., Middleboro, Mass), at 25° C. and a shear rate of 1 to 120 second-1 (e.g., 21 second-1).

The viscosity can be adjusted for better delivery and/or greater stability using a thickening agent (i.e., a viscosity control agent). As used herein, the term "thickening agent" means any material known or otherwise effective in providing suspending, gelling, viscosifying, solidifying or thickening properties to the composition or which otherwise provide structure to the final product form. These thickening agents may include gelling agents, polymeric or nonpolymeric agents, inorganic thickening agents, or viscosifying agents. The thickening agents may include organic solids, silicone solids, crystalline or other gellants, inorganic particulates such as clays or silicas, or combinations thereof. The preferred thickening agent is an acrylate/$C_{10-30}$ alkyl acrylate crosspolymer.

Examples can be found in WO2018053356A1. Those agents include acrylate copolymers, cationic acrylamide copolymers, polysaccharides, etc.

Commercially available acrylate copolymers include those under the trade name ACULYN™ (from Dow Chemical Company) such as ACULYN™ 22 (a copolymer of acrylates and stearth-20 methacrylate), ACULYN™ 28 (a copolymer of acrylate and beheneth-25 methacrylate), ACULYN™ 33 (a copolymer of acrylic acid and acrylate), ACULYN™ 38 (a crosspolymer of acrylate and vinyl neodecanoate), and ACULYN™ 88 (a crosspolymer of acrylate and steareth-20 methacrylate). Other suitable acrylate copolymers are available under the trade name of Carbopol® such as Carbopol® ETD 2020 polymer (a crosspolymer of acrylate and C10-C30 alkyl acrylate), Carbopol® ETD 2691, Carbopol® ETD 2623 (a crosslinked acrylate copolymer). Their molecular weight ranges from 100000 to 3,000,000 (Carbomer 672, M.W. 3,000,000; Carbomer 910, M.W., 750,000; Carbomer 934, M.W., 500000; Carbomer 940, M.W. 4000000; Carbomer 941, M.W. 1250000; and Carbomer 1662, M.W., 4,000,000). Carbomer polymers are commercially available, e.g., under the trade name Carbopol® from Lubrizol Corporation.

Suitable polysaccharides used as viscosity controlling agents include starches, pectin, and vegetable gums such as alginin, guar gum, locust bean gum, and xanthan gum (e.g., under trade name of Keltrol® T, commercially available from CP Kelco, Atlanta, Georgia).

Cationic acrylamide copolymers preferably are copolymers of acrylamide and methacrylate cross-linked with a difunctional vinyl addition monomer, such as methylene bisacrylamide. Particularly preferred polymers are copolymers of 20% acrylamide and 80% MADAM methyl chloride (MADAM: dimethyl amino ethyl methacrylate) cross-linked with from 450 to 600 ppm of methylene bisacrylamide. See U.S. Pat. No. 8,242,215. Such materials are commercially available from SNF Floerger under the trade names Flosoft™ FS 200, Flosoft™ FS 222, and Flosoft™ FS 228.

Additional examples of the viscosity control agent include polypropylene glycol, materials containing propylene oxide groups, materials containing polyethylene oxide groups, polysorbate 20 (TWEEN™ 20), POLOXAMER™ 124 (PLURONIC™ L44) polyethylene oxide-polypropylene oxide block copolymer having the formula (EO)x(PO)y (EO)z with x=11±3, z=11±3 and y=21±5, POLOXAMER™ L35, POLOXAMER™ L31, polyethylene glycol 55 (PEG-55), glycerin, diethylene glycol, CREMOPHOR™ polyoxyethyleneglyceroltriricinoleat, GLUCAM™ P-10 propylene glycol ether of methyl glucose with 10 polypropylene oxide units, PLURIOL™ E300 alkoxylates based on ethylene oxide and propylene oxide, sodium cumene sulfonate (SCS), sodium xylene sulfonate (SXS), GLUCAM™ P-20 propylene glycol ether of methyl glucose with 20 polypropylene oxide units, GLUCAM™ E-20 ethylene glycol ether of methyl glucose with 20 polyethylene oxide units, GLUCAM™ E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. More viscosity control agents are described in U.S. Pat. No. 6,465,416 and US 20060252668.

The molecular weight of the polymeric viscosity control agent varies from 1000 to 10000000 (e.g., 2000 to 6000000, 3000 to 5000000, 10000 to 5000000, and 50000 to 5000000).

The amount of the viscosity control agent can be any desired amount to obtain the desired viscosity of the composition. In certain embodiments, the amount is 0.01% to 5% (e.g., 0.1% to 5%, 0.2% to 4%, and 0.3% to 2%) by weight of the composition.

Surfactants

The liquid fragrance compositions of this invention contain a surfactant. The preferred surfactant is glyceryl ricinoleate. It is unexpectedly found that this surfactant stabilizes the liquid fragrance compositions even when used in an amount of 0.2 wt % or greater (e.g., 0.3 wt % or greater, 0.4 wt % or greater, 0.5 wt % or greater, 0.2 wt % to 20 wt %, 0.3 wt % to 15 wt %, 0.4 wt % to 10 wt %, 0.5 wt % to 5 wt %, 0.5 wt % to 3 wt %, and 0.5 wt % to 2.5 wt %) by weight of the liquid fragrance composition. The amount of glyceryl ricinoleate preferably has a range of from a lower limit of 0.2 wt %, 0.3 wt %, 0.4 wt %, 0.5 wt %, 0.6 wt %, 0.7 wt %, 0.8 wt %, 1 wt %, or 1.2 wt % to an upper limit of 30 wt %, 20 wt %, 15 wt %, 10 wt %, 8 wt %, 7 wt %, 6 wt %, 5 wt %, 4 wt %. 3 wt %, 2.5 wt %, 2 wt %, 1.5 wt %, or 1.2 wt %.

The liquid fragrance composition can also contain other suitable surfactants such as amphoteric surfactants, anionic surfactants, cationic surfactants, and non-ionic surfactant. These surfactants can be present at 0.01% to 20% (e.g., 0.05% to 10%, 0.1% to 5%, and 0.5% to 3%) by weight of the liquid fragrance composition.

As used herein, the term "amphoteric surfactant", and grammatical variations thereof, refers to surfactants that have both acidic and basic character. In particular, the term refers to surfactants that contain an acidic group and a basic nitrogen-containing group, as described in detail in Amphoteric Surfactants, Second Edition, E. G. Lomax (Ed.) Marcel Dekker, Inc., New York (1996), the relevant disclosures of which are incorporated herein by reference (hereinafter "Lomax"). The basic nitrogen-containing group can be either weakly basic or strongly basic. Weakly basic nitrogen-containing groups include primary, secondary and tertiary amino groups, which can be either neutral or cationic, depending on the pH of the medium in which the surfactant is present. Strongly basic nitrogen-containing groups include quaternary ammonium groups, which are cationic at all pH values. Amphoteric surfactants include zwitterionic surfactants such as betaines. As used herein and in the appended claims, the term "betaine" and grammatical variations thereof includes alkyl betaines, alkylamido betaines, sulfobetaines, sulfito betaines, sulfato betaines, phosphinate betaines, phosphonate betaines, phosphito betaines, phosphato betaines, sulfonium betaines, and phosphenium betaines.

The acidic groups of the amphoteric surfactants, as defined herein include carboxylic acids, sulfonic acids, phosphonic acids, and like acid groups.

Other suitable amphoteric surfactants include amino acid amphoterics, such as amino carboxylic acids and amino sulfonic acids as described in detail in Chapter 2 of Lomax; betaines, such as alkyl betaines, alkylamido betaines, sulfobetaines, sulfito betaines, sulfato betaines, phosphinate betaines, phosphonate betaines, phosphito betaines, phosphato betaines, sulfonium betaines, phosphenium betaines, and the like, as described in detail in Chapter 3 of Lomax; imidazoline derived amphoterics, such as described in detail in Chapter 4 of Lomax; and alkyl polyamino amphoterics, such as fatty polyamine carboxylates, acyl polyethylene amine carboxylates, and the like, as described in detail in Chapter 5 of Lomax. Specific examples include lauramidopropyl betaine, myristamidopropyl betaine, palmitamidopropyl betaine, cocamidopropyl betaine, palm kernelamidopropyl betaine, babassuamidopropyl betaine, cocobetaine, lauryl betaine, myristyl betaine, cetyl betaine, cocamidopropyl hydroxysultaine, lauramidopropyl hydroxysultaine, palm kernelamidopropyl hydroxysultaine, babassuamido-propyl hydroxysultaine, myristamidopropyl hydroxysultaine, and a combination thereof.

As used herein, the term "anionic surfactant" and grammatical variations thereof, refers to a surfactant in which the hydrophilic portion of the surfactant carries no charge unless the pH is elevated to neutrality or above. Anionic surfactants include the chemical classes of: acylamino acids (and salts), such as acylglutamates, acyl peptides, sarcosinates, taurates, etc.; carboxylic acids (and salts), such as alkanoic acids (and alkanoates), ester carboxylic acids, ether carboxylic acids, and the like; phosphoric acid esters (and salts); sulfonic acids (and salts), such as acyl iscthionates, alkylaryl sulfonates, alkyl sulfonates, alkyl sulfosuccinates (and salts), and the like; and sulfuric acid esters, such as alkyl ether sulfates, alkyl sulfates, and the like. A description of anionic surfactants can be found in numerous texts and monographs, such as Rieger, Surfactant Encyclopedia, 2nd Ed., C&T Ingredient Resource Series of COSMETICS AND TOILETRIES® magazine, published by Allured Publishing Corporation, Carol Stream, Ill. (1996), the relevant disclosures of which are incorporated by reference. Specific examples include an alkyl sulfonate, especially a $C_{12-16}$ alpha olefin sulfonate (AOS), an alkyl sulfate, an alkyl ether sulfate, an alkylaryl sulfonate, an alkyl sulfosuccinate, a combination thereof and salts thereof.

As used herein, the term "nonionic surfactant" and grammatical variations thereof, refers to a surfactant in which the hydrophilic portion of the surfactant carries no charge under acidic, neutral, or basic conditions. Examples include water-soluble condensation products of a $C_8$-$C_{20}$ alkanol with a heteric mixture of ethylene oxide and propylene oxide. Such surfactants are commercially available from BASF-Wyandotte. Nonionic surfactants under the trade name Plurafac® (e.g., Plurafac® LF300) are condensation products of a primary alkanol having 9 to 18 carbon atoms with 1 to 5 moles of ethylene oxide and 1 to 5 moles of propylene oxide. The nonionic synthetic organic surfactants generally are the condensation products of an organic aliphatic or alkyl aromatic hydrophobic compound and hydrophilic ethylene oxide groups.

Examples of the nonionic surfactant include Neodol ethoxylates (Shell Co.), which are higher aliphatic, primary alcohol containing about 9-15 carbon atoms, such as $C_9$-$C_{11}$ alkanol condensed with 2.5 to 10 moles of ethylene oxide (NEODOL 91-2.5 OR-5 OR-6 OR-8), $C_{12}$-13 alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like.

Other nonionic system comprises the mixture of a nonionic surfactant formed from a $C_9$-$C_{11}$ alkanol condensed with 2 to 3.5 moles of ethylene oxide ($_{C9-11}$ alcohol EO 2 to 3.5:1) with a nonionic surfactant formed from a $C_9$-$C_{11}$ alkanol condensed with 7 to 9 moles of ethylene oxide ($C_9$-$C_{11}$ alcohol EO 7 to 9:1), wherein the weight ratio of the $C_9$-$C_{11}$ alcohol EO 7 to 9:1 to the $C_9$-$C_{11}$ alcohol EO 2 to 3.5:1 is from 4:1 to 1:1 from preferably 3.5:1 to 2:1.

Additional satisfactory water soluble alcohol ethylene oxide condensates are the condensation products of a secondary aliphatic alcohol containing 9 to 18 carbon atoms in a straight or branched chain configuration condensed with 5 to 30 moles of ethylene oxide. Examples of commercially available nonionic detergents of the foregoing type are CH-Cis secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

The ethoxylated alkyl ester nonionic surfactants are commercially available under the trademarks of Genagen™ 24 and Genagen™81.

More exemplary nonionic surfactants are polypropylene glycols such as dipropylene glycol and polypropylene glycol having a molecular weight of 150 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate.

Useful cationic surfactants are of the single long chain alkyl quaternary ammonium type, having one alkyl chain which contains an average of from about 20 to about 30 carbon atoms, preferably from about 20 to about 25 carbon atoms, and most preferably from about 20 to about 22 carbon atoms. An example of such a compound, made from a naturally-occurring material, is a rapeseed oil-derived tri-methyl quaternary ammonium material. An especially preferred cationic material for use herein is the single long chain alkyl $C_{20-22}$ quaternary ammonium compound sold under the tradename Genamin KDM, by American Hoechst Corp. The remaining groups attached to the quaternary nitrogen atom are preferably $C_1$-$C_4$ alkyl (especially methyl or ethyl groups) or hydroxyalkyl groups, or a benzyl group, as long as no more than one such benzyl group is contained per molecule.

Examples of cationic surfactants useful herein include eicosyl alkyl ($C_{20}$) trimethyl (or triethyl, methyldiethyl, or methyldihydroxyethyl) ammonium chloride (or methyl sulfate), docosyl ($C_{22}$) alkyl trimethylammonium chloride (or methyl sulfate), $C_{20-22}$ alkyl trimethylammonium chloride (or methyl sulfate), methyl (1) eicosylalkyl amido ethyl (2) methyl imidazolinium chloride (or methyl sulfate), methyl (1) hydroxyethyl amido ethyl (2) docosylalkyl imidazolinium methyl sulfate (or bromide), or mixtures of those surfactants.

Additional examples of suitable surfactant can be found in U.S. Pat. No. 7,256,164.

pH

Preferably, the liquid fragrance compositions of this invention have a pH value of 3.5 to 8 (more preferably 4 to 5 such as 4.5). At this pH range, it was surprisingly found that the compositions were stable.

The pH can be adjusted using a basic or acidic material such as sodium hydroxide, potassium hydroxide, ammonium hydroxide, sodium carbonate, potassium bicarbonate, hydrochloric acid, acetic acid, etc.

Fragrances

The fragrance contained in the composition can be an encapsulated or free fragrance. A free fragrance refers to a neat fragrance essentially free of a fragrance carrier. It is not encapsulated or enclosed within a polymeric network, or otherwise immobilized in a delivery system.

Suitable fragrances and raw materials are described in International Application Publication WO2015/023961A1 and US Application Publication US2014/0287008A1.

The liquid fragrance compositions of this invention can have a content of a fragrance such as 3 wt % to 40 wt % (e.g., 4 wt % to 30 wt %, 5 wt % to 25 wt %, and 7 wt % to 20 wt %) with a lower limit of 3 wt %, 4 wt %, 5 wt %, 6 wt %. 7 wt %, 8 wt %, 9 wt %, 10 wt %, or 12 wt % and an upper limit of 40 wt %, 30 wt %, 25 wt %, 20 wt %, 18 wt %, 16 wt %, or 15 wt %.

Preferably, the fragrance contains by weight of the fragrance 10 wt % or less of one or more Type (IV) fragrance ingredients. The term "Type (IV) fragrance ingredient" refers to a fragrance ingredient compound having a primary hydroxyl group. Examples include hexanol and octanol. The term "primary hydroxyl group" refers to a hydroxyl group (—OH) connected to a primary carbon atom such as in a "—$CH_2OH$" group.

In some embodiments, the fragrance contains the following components: (i) 0 wt % to 10 wt % of one or more Type (I) fragrance ingredients having a ClogP of less than 2, (ii) 80 wt % to 100 wt % of one or more Type (II) fragrance ingredients having a ClogP of 2 to 5, and (iii) 0 wt % to 20 wt % of one or more Type (III) fragrance ingredients having a ClogP of greater than 5. It is unexpectedly found that liquid fragrance compositions prepared from these fragrances are stable and have a high fragrance intensity when incorporated into consumer products.

In other embodiments, it is preferred that the fragrance having a weight-averaged ClogP of 2 to 7 (e.g., 2.5 to 6, and 2.5 to 5). The weight-averaged ClogP is calculated as follows:

$$ClogP=\{Sum[(Wi)(ClogP)i]\}/\{Sum\ Wi\},$$

in which Wi is the weight fraction of each fragrance ingredient and (ClogP)i is the ClogP of that fragrance ingredient.

Those with skill in the art will appreciate that many fragrances can be created employing various solvents and fragrance chemicals.

The term "log P" refers to the octanol-water partition coefficient (P) of a material, i.e., the ratio of a material's equilibrium concentration in octanol and water, which is well-known in the literature as a measure of hydrophobicity and water solubility (see, Leo, et al. (1971) Chem. Rev. 71:526-616; Hansch, et al. (1968) J. Org. Chem. 33:347-350). The "calculated log P" (ClogP) is determined by the fragment approach of Hansch and Leo (cf., A. Leo, in Comprehensive Medicinal Chemistry, Vol. 4, C. Hansch, P G Sammens, J. B. Taylor, and C. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

In some embodiments, the weight ratio between the fragrance and glyceryl ricinoleate is from 1:1 to 28:1 (e.g., 2:1 to 28:1) with a lower limit of 1:1, 2:1, 3:1, 4:1.5:1, or 7:1 and an upper limit of 28:1, 25:1, 20:1, 18:1, 16:1 or 15:1.

Microcapsules

The liquid fragrance compositions of this invention can contain microcapsules having a core and a microcapsule wall encapsulating the core. The core has a fragrance and/or a malodor counteractant. The wall is formed of a polymer such as a urea-formaldehyde polymer, a melamine-formaldehyde polymer, a phenolic-formaldehyde polymer, a urea-glutaraldehyde polymer, a melamine-glutaraldehyde polymer, a phenolic-glutaraldehyde polymer, polyurea, polyurethane, polyacrylate, polyamide, polyester, an epoxy cross-linked polymer, a polyfunctional carbodiimide cross-linked polymer, silica, a silica-derived material, polysiloxanes, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and combinations of these materials. Other suitable polymeric materials are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, microcapsules can be made via the simple or complex coacervation of gelatin. Preferred encapsulating wall polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts.

Preparation of microcapsules is described in WO 2004/054362; U.S. Pat. Nos. 10,092,486, 8,299,011, and 7,833,960.

pH Modifiers

In some embodiments, one or more pH modifiers are included in the fragrance composition to adjust the pH value to 3.5 to 8. Exemplary pH modifiers include metal hydroxides (e.g., LiOH, NaOH, KOH, and $Mg(OH)_2$), metal carbonates and bicarbonates ($CsCO_3$, $Li_2CO_3$, $K_2CO_3$, $NaHCO_3$, and $CaCO_3$), metal phosphates/hydrogen phosphates/dihydrogen phosphates, metal sulfates, ammonia, mineral acids (HCl, $H_2SO_4$, $H_3PO_4$, and $HNO_3$), carboxylic acids (e.g., acetic acid, citric acid, lactic acid, benzoic acid, and sulfonic acids), and amino acids.

Neutralizing agents can also be used as pH modifiers. Exemplary neutralizing agents include triethylamine, 2-amino-2-methyl-1-propanol (commercially available from Dow Chemical, Midland, Michigan), Triisopropanolamine (commercially available from Dow Chemical), tetrahydroxypropyl ethylene diamine (commercially available under the trademark of Neutrol® TE from BASF, Florham Park, New Jersey), polyoxyethylene (15) cocoalkylamine (commercially available under the trademark of Ethomeen® C/25 from Nouryon, Bridgewater, New Jersey), bis(2-hydroxyethyl)soyaalkylamine (commercially available under the trademark of Ethomeen® SV/12 from Nouryon), octadecyl dimethyl amine (commercially available under the trademark of Armeen® DM18D from Nouryon), polyethylene glycol-based amines, poly(diallyldimethylammonium chloride) (PQ-6), and copolymer of vinylpyrrolidone and quaternized dimethylaminoethyl methacrylate (PQ-11).

Typically, the fragrance composition contains a pH modifier (e.g., a neutralizing agent) at a level of 0.001% to 4% (e.g., 0.01% to 3%, 0.02% to 2%, and 0.05% to 1%).

Active Ingredients

The liquid fragrance of the invention may contain one or more active materials. Nonlimiting examples include those described in US 20180256627 and US20170020796, which are incorporated by reference. These active material include flavor ingredients, taste masking agents, taste sensates, malodor counteracting agents, vitamins, antibacterials, sunscreen actives, antioxidants, anti-inflammatory agents, anesthetics, analgesics, antifungal agents, antibiotics, anti-viral agents, anti-parasitic agents, anti-infectious and anti-acne agents, dermatological active ingredients, enzymes and co-enzymes, skin whitening agents, anti-histamines, chemotherapeutic agents, and insect repellents. In addition to the active materials listed above, the products of this invention can also contain dyes, colorants or pigments, naturally obtained extracts (for example paprika extract and black carrot extract), and aluminum lakes. In some embodiments, the amount of active material in the liquid composition is from 0.1 to 95% (e.g., 0.5 to 10%, 1 to 90%, 2% to 80%, 4 to 70%, and 5 to 50%) by weight of the composition.

Other Adjunct Materials

One or more additional rheology modifiers (e.g., a second, third, or fourth rheology modifier) are optionally added at a level of 0.001 wt % to 10 wt % of the fragrance composition. They may be polymeric or colloidal (e.g., modified cellulose polymers such as methylcellulose, hydoxyethylcellulose, hydrophobically modified hydroxyethylcellulose, and cross-linked acrylate polymers such as Carbomer, hydrophobically modified polyethers). Optionally, silicas, either hydrophobic or hydrophilic, can be included at a concentration from 0.01 wt % to 20 wt %, more preferable from 0.5 wt % to 5 wt %, by the weight of the capsule composition. Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPERNAT 22S, SIPERNAT 50S (available from Degussa), and SYLOID 244 (available from Grace Davison).

One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like. Further suitable humectants, as well as viscosity control/suspending agents, are disclosed in U.S. Pat. Nos. 4,428,869, 5,500,223, and 6,930,078, The fragrance composition can also contain one or more structural agents including nonionic, anionic, cationic, and amphoteric polymers, such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives, gums of microbial origin (e.g., xanthan gum, scleroglucan gum, etc.), and gums derived from plant exudates (e.g., gum arabic, carrageenan gum, agar gum and carob gum), pectins, alginates, and starches. Additional examples include Carbopol® ETD-2020 (acrylic acid/$C_{10}$-C30 alkyl methacrylate crosslinked copolymer); Carbopol® 1382, Ultra-Thix™ P-100 by Ashalnd and the ACULYN™ 22, 28, 44 and 46N sold by Dow Chemical.

Other examples include anionic thickening polymers sold by the company ALLIED COLLOIDS under the names SALCARE® SC 80 and SALCARE® SC 90, aqueous emulsions containing 30% of a crosslinked terpolymer of methacrylic acid, of ethyl acrylate and of steareth-10-allyl ether (40/50/10).

Other suitable structural agents are anionic thickening polymers containing at least one fatty chain such as (1) maleic anhydride/$C_{30-38}$-α-olefin/isopropyl maleate copolymer sold under the name PERFORMA® 1608 from NEW-PHASE TECHNOLOGIES; (2) acrylic terpolymers formed from: (a) 20% to 70% by weight of a carboxylic acid with α,β-monoethylenic unsaturation; (b) 20% to 80% by weight of a nonsurfactant monomer with α,β-monoethylenic unsaturation different from (a); and (c) 0.5% to 60% by weight of a nonionic monourethane;

Another class named associative polymers include polyurethanes, cellulose derivatives which are cationic or nonionic, associative vinyllactams, associative unsaturated polyacids, associative aminoplast ethers, and associative polymers or copolymers containing at least one monomer comprising ethylenic unsaturation. A representative example of an associative polyurethane terpolymer as a 25 percent aqueous dispersion, known by the trade name, Viscophobe® DB 1000 and commercially available from Amerchol. Representative examples of associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof. Representative examples of quaternized alkylhydroxy-ethylcelluloses containing a $C_8$-C30 hydrophobic chain include commercial products under the trademarks of Quatrisoft® LM 200, Quatrisoft® LM-X 529-18-A, Quatrisoft® LM-X 529-18B ($C_{12}$ alkyl) and Quatrisoft® LM-X 529-8 (C18 alkyl) sold by Amerchol and the products Crodacel® QM, Crodacel® QL (C1-2 alkyl) and Crodacel® QS (C18 alkyl) sold by Croda. Representative examples of nonionic cellulose derivatives include hydroxyethylcelluloses modified by groups comprising at least one hydrophobic chain, such as alkyl, arylalkyl or alkylaryl groups, or their blends, such as the product Natrosol® Plus Grade 330 CS (C1-6 alkyls) sold by Aqualon or the product Bermocoll® EHM 100 sold by Berol Nobel.

Associative polyvinyllactams, representative examples include poly(vinyllactam) polymers, of Vinylpyrrolidone/ dimethylaminopropylmethacrylamide dodecyldimethyl methacryl amidopropylammonium tosylate terpolymers, vinylpyrroidone/dimethylaminopropyl methacrylamide cocoyl dimethyl methacryl amidopropylammonium tosylate terpolymers or vinylpyrrolidone dimethyl aminopropyl methacryl amide/lauryldimethylmethacrylamidopropyl-ammonium tosylate or chloride terpolymers. The vinyl pyrrolidone/dimethylaminopropyl-methacrylamide/lauryldimethyl methacryl amido propyl ammonium chloride terpolymer by Ashalnd under the name Styleze® W20.

Examples of associative polymers comprising an aminoplast ether backbone include commercial products under the trademarks of Pure-Thix® L, Pure-Thix® M, Pure-Thix® HH, Pure-Thix® TX-1442, and Sepimax™ Zen.

The inorganic/mineral like structural agents include clays, fumed silicas and specialty clays. Common types of modified and unmodified inorganic rheology modifiers are attapulgite clays, bentonite clays, organoclays, and synthetic silicas. They usually function as suspending or gelling agents. Inorganic rheology modifiers are thixotropes. Some mineral types are useful for thickening aqueous systems and others for solvent-based coatings. It depends mostly on the thickener's particle surface, which can be organically modified to render it hydrophobic for solvent-based coatings. Inorganic rheology modifiers are sometimes added to aqueous formulations as secondary thickeners to improve the anti-sag, anti-settling and anti-synerisis properties of a formulation. Examples are Efka® RM1900 and 1920 from BASF, Rheoluxe® 880, 812, 8015, Bentone® SD-1, Bentone® Gel MSO V/ABO/IHD V, Hectorite organoclays from Elementis, Laponite® XLG, XR, XLS, XL21, D by BYK Chemie etc.

The liquid fragrance compositions of this invention are suitable for use in many applications as listed below.
Applications. The liquid fragrance compositions of the present invention are well-suited for use, without limitation, in the following applications:
a) Laundry. The liquid fragrance compositions can be added to a laundry washing machine or wash basin, with or without a liquid or powder detergent. They can be added before a laundry cycle, during soaking, washing, or rinsing, or before removing the laundry for drying.
b) The liquid fragrance compositions can also be added to a dryer, with or without fabric conditioners, tumble drier sheets, fabric refreshers, fabric refresher sprays, and fabric softener systems such as those described in U.S. Pat. Nos. 6,335,315.
c) The liquid fragrance compositions can be added to an automatic dish washer or a hand dish washing basin, with or without a liquid/solid dish detergents including Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562

The liquid fragrance compositions can also be added to the following products:
d) All-purpose Cleaners including bucket dilutable cleaners and toilet cleaners
e) Bathroom Cleaners
f) Bath Tissue
g) Rug Deodorizers
  i. Candles
  ii. Room Deodorizers
  iii. Floor Cleaners
  iv. Disinfectants
  v. Window Cleaners
  vi. Garbage bags/trash can liners
  vii. Air Fresheners including room deodorizer and car deodorizer, scented candles, sprays, scented oil air freshener, Automatic spray air freshener, and neutralizing gel beads
  viii. Moisture absorber
  ix. Household Devices such as paper towels and disposable Wipes
  x. Moth balls/traps/cakes
h) Baby Care Products
  i. Diaper Rash Cream/Balm
  ii. Baby Powder
i) Baby Care Devices
  i. Diapers
  ii. Bibs
  iii. Wipes
j) Oral Care Products such as oral rinses
k) Health Care Devices
  i. Dental Floss
  ii. Toothbrushes
  iii. Respirators
  iv. Scented/flavored condoms
l) Feminine Hygiene Products such as Tampons, Feminine Napkins and Wipes, and Pantiliners
m) Personal Care Products: Perfumes, Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Alcohol free perfume
  x. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
  xi. Wax-based Deodorant. An exemplary formulation as follows:
    1. Parafin Wax 10-20%
    2. Hydrocarbon Wax 5-10%
    3. White Petrolatum 10-15%
    4. Acetylated Lanolin Alcohol 2-4%
    5. Diisopropyl Adipate 4-8%
    6. Mineral Oil 40-60%
    7. Preservative (as needed)
      The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.

xii. Glycol/Soap Type Deodorant. An exemplary formulation as follows:
1. Propylene Glycol 60-70%
2. Sodium Stearate 5-10%
3. Distilled Water 20-30%
4. 2,4,4-Trichloro-2'-Hydroxy Diphenyl Ether, manufactured by the Ciba-Geigy Chemical Company and a Trademark of the Ciba-Geigy Chemical Company) 0.01-0.5%

The ingredients are combined and heated to 75° C. with stirring until the sodium stearate has dissolved. The resulting mixture is cooled to 40° C. followed by addition of a composition of this invention.

xiii. Lotion including body lotion, facial lotion, and hand lotion
xiv. Body powder and foot powder
xv. Toiletries
xvi. Body Spray
xvii. Shave cream and male grooming products
xviii. Bath Soak
xix. Exfoliating Scrub n) Personal Care Devices
   i. Facial Tissues
   ii. Cleansing wipes o) Hair Care Products
   i. Shampoos (liquid and dry powder)
   ii. Hair Conditioners (Rinse-out conditioners, leave-in conditioners, and cleansing conditioners)
   iii. Hair Rinses
   iv. Hair Refreshers
   v. Hair perfumes
   vi. Hair straightening products
   vii. Hair styling products, Hair Fixative and styling aids
   viii. Hair combing creams
   ix. Hair wax
   x. Hair foam, hair gel, nonaerosol pump spray
   xi. Hair Bleaches, Dyes and Colorants
   xii. Perming agents
   xiii. Hair wipes p) Beauty Care
   i. Fine Fragrance—Alcoholic and non-alcoholic. Compositions and methods for incorporating fragrance capsules into alcoholic fine fragrances are described in U.S. Pat. No. 4,428,869. Fine fragrances may contain the following:
      1. Ethanol (0-99%)
      2. Water (0-99%)
      3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0-1%)
      4. Optionally an emulsifier or an emollient may be included including but not limited to those listed above
   ii. Solid Perfume
   iii. Lipstick/lip balm
   iv. Make-up cleanser
   v. Skin care cosmetic such as foundation, pack, sunscreen, skin lotion, milky lotion, skin cream, emollients, skin whitening
   vi. Make-up cosmetic including manicure, mascara, eyeliner, eye shadow, liquid foundation, powder foundation, lipstick and cheek rouge q) Consumer goods packaging such as fragranced cartons, fragranced plastic bottles/boxes r) Pet care products
   i. Cat litter
   ii. Flea and tick treatment products
   iii. Pet grooming products
   iv. Pet shampoos
   v. Pet toys, treats, and chewables
   vi. Pet training pads
   vii. Pet carriers and crates All parts, percentages and proportions refer to herein and in the claims are by weight of the liquid fragrance composition unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The term "glyceryl ricinoleate" refers to the monoester of glycerin and ricinoleic acid, namely 2,3-dihydroxypropyl-12-hydroxyoctadec-9-enoate including E-Z isomers, enantiomers, diastereomers and mixtures thereof in any weight ratio, such as (9Z,12R)— and (9E,12R)-isomers. This compound can be represented by the following structure:

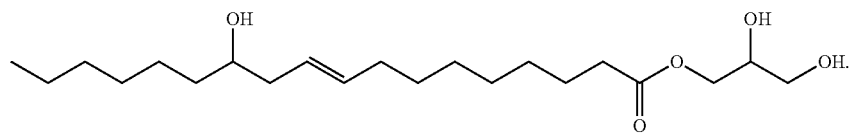 [SMILES: CCCCCCC(O)C/C=C/CCCCCCCC(=O)OCC(O)CO]

The invention is described in greater detail by the following non-limiting examples. Without further elaboration, it is believed that one skilled in the art can, based on the description herein, utilize the present invention to its fullest extent. All publications cited herein are incorporated by reference in their entirety.

EXAMPLES

The liquid fragrance composition of the invention can be prepared as follows:
1) mixing glyceryl ricinoleate (surfactant available under the trademark of Softigen® 701 from IOI Oleo GmbH, Germany) and a fragrance for 5 minutes or until homogeneous to obtain a fragrance oil solution,
2) adding under agitation to the fragrance oil solution acrylates/$C_{10-30}$ alkyl acrylate crosspolymer (a thickening agent, commercially available under the trademark of Carbopol® Ultrez 21 from Lubrizol, Wickliffe, Ohio) to obtain a fragrance dispersion, 3) under shear, adding the fragrance dispersion to water with a neutralizing agent (such as sodium hydroxide NaOH) to form a fragrance mixture, and 4) allowing the fragrance mixture to age with agitation until the thickening agent is fully hydrated to obtain the liquid fragrance composition.

Examples 1 and 2

Table 1 below shows the formula of two liquid fragrance compositions of this invention, i.e., Example-1 and Example-2. The table also shows the formula of two comparative compositions, i.e., Comp-1 and Comp-2. Comp-1 contained polyethylene glycol sorbitan monolaurate (commercially available under the trademark of Tween® 20, Sigma Aldrich, St. Louis, MO) instead of glyceryl ricinoleate. Comp-2 contained polyglyceryl-6 polyricinoleate instead of glyceryl ricinoleate.

TABLE 1

| Ingredient | Example-1 | Comp-1 | Example-2 | Comp-2 |
|---|---|---|---|---|
| Research Fragrance A, wt % | 14 | 14 | 15 | 15 |
| glyceryl ricinoleate, wt % | 0.7 | 0 | 1 | 0 |
| polyethylene glycol sorbitan monolaurate, wt % | 0 | 0.7 | 0 | 0 |
| Polyglyceryl-6 polyricinoleate, wt % | 0 | 0 | 0 | 1 |
| acrylates/$C_{10-30}$ alkyl acrylate crosspolymer, wt % | 0.3 | 0.3 | 0.3 | 0.3 |
| Water, wt % | 85 | 85 | 83.7 | 83.7 |
| Stable after 8 weeks? | YES | NO | YES | NO |

The acrylates/$C_{10-30}$ alkyl acrylate crosspolymer, a thickening agent, is commercially available under the trade name of Carbopol® Ultrez 21 from Lubrizol, Wickliffe, Ohio.

Example 2 had a pH of 4.12 and a viscosity of 1033 cP.

The compositions of this invention were stable after stored at 25° C. for 8 weeks. By contrast, Comp-1 and Comp-2 were unstable with fragrance oil separation under the same storage conditions. The stability were measured at 4° C., 25° C., 37° C., and 50° C. in a 4-oz glass jar. A composition is deemed stable if no phase separation is observed after 12 weeks.

Examples 3-8

Table 2 below shows the formula of six liquid fragrance composition of this invention, i.e., Example-3 to Example-8. The table also shows the formula of two comparative compositions, i.e., Comp-3 and Comp-4.

The compositions of this invention Example-3 to Example-8 were stable after stored at 25° C. for 8 weeks. By contrast, Comp-3 was unstable with fragrance oil separation under the same storage conditions. In Comp-4, a homogeneous suspension could not be formed due to the low amount of surfactant as compared to the fragrance.

All samples listed in Table 2 contained a preservative, available under the trade name of Acticide® MBS2550 from Thor Specialties, Inc., Shelton, Connecticut. This preservative contains 5% of 1,2-benzisothiazol-3(2H)-one, 2.5% of 2-methylisothiazol-3(2H)-one, and 92.5% of inert ingredients, all by weight of the preservative.

TABLE 2

| EXAMPLE | 3 | 4 | 5 | 6 | 7 | 8 | Comp-3 | Comp-4 |
|---|---|---|---|---|---|---|---|---|
| Fragrance/glyceryl ricinoleate | 14:10 | 5:1 | 10:1 | 14:1 | 20:1 | 28:1 | 40:1 | 60:1 |
| Research Fragrance A, wt % | 14 | 5 | 10 | 14 | 20 | 14 | 40 | 60 |
| glyceryl ricinoleate, wt % | 10 | 1 | 1 | 1 | 1 | 0.5 | 1 | 1 |
| acrylates/$C_{10-30}$ alkyl acrylate crosspolymer, wt % | 0.3 | 0.3 | 0.3 | 0.3 | 0.3 | 0.3 | 0.3 | 0.3 |
| Preservative, wt % | 0.4 | 0.4 | 0.4 | 0.4 | 0.4 | 0.4 | 0.4 | 0.4 |
| Water (with 0.07% NaOH), wt % | 75.3 | 93.3 | 88.3 | 84.3 | 78.3 | 84.8 | 58.3 | 38.3 |

Example 9

Table 3 below shows the formula of a liquid fragrance composition of this invention, i.e., Example-9. This composition contained a melamine-formaldehyde (MF) microcapsule commercially available as a slurry from International Flavors & Fragrances (Union Beach, New Jersey). The MF microcapsule contained 28% of a fragrance in the microcapsule core by weight of the microcapsule slurry.

TABLE 3

| | |
|---|---|
| Research fragrance B, wt % | 15 |
| MF microcapsule, wt % | 35 |
| glyceryl ricinoleate, wt % | 0.6 |
| acrylates/C10-30 alkyl acrylate crosspolymer, wt % | 0.25 |
| Water, wt % | 49.15 |

Example 10

A liquid fragrance composition, Example-10, was prepared using the components in Table 4 below.

TABLE 4

| Ingredients | Wt % |
|---|---|
| Research fragrance A, wt % | 14 |
| glyceryl ricinoleate, wt % | 0.7 |
| acrylates/C10-30 alkyl acrylate crosspolymer, wt % | 0.25 |
| Acticide ® MBS2550* | 0.4 |
| Water, wt % | 84.65 |

*Acticide ® MBS 2550, trademark of Thor Specialities.

The liquid fragrance composition Example-10 (2 g) was added to 2000 g of a bucket diluatable cleaner (commercially available under the trade name of Fabuloso™ from Colgate-Palmolive, Piscataway Township, New Jersey) to obtain Sample-10. The liquid fragrance composition improved the fragrance longevity, room fill and malodor coverage.

A commercial cleaner, i.e., Crisp Water Aerosol from SC Johnson (Racine, WI) was used as control.

The fragrance intensity was evaluated by an expert panel at initial, 5 minutes, 10 minutes and 15 minutes after spraying the cleaner. The intensity was measured at a scale of 0 to 9 with o as non-detected and 9 as the strongest).

The fragrance intensities were shown in Table 5 below.

TABLE 5

|  | Crisp Water | Sample 10 |
|---|---|---|
| Initial | 6 | 7 |
| 5 minutes | 5 | 3 |
| 10 minutes | 1 | 3 |
| 15 minutes | 0.25 | 3 |

Example 11

The liquid fragrance composition, Example-1, was added to an alcohol-free perfume body cream at a neat oil loading of 15%. The scented perfume body cream was applied to skin. Unexpectedly, it had a longer lasting fragrance and a better skin feel as compared to an Eau De Toilette product having the same fragrance at 15% loading.

What is claimed is:

1. A liquid fragrance composition comprising:
   (i) 3 wt % to 40 wt % of a fragrance,
   (ii) 0.5 wt % to 5 wt % of glyceryl ricinoleate, and
   (iii) 60 wt % to 95 wt % of water,
   wherein the weight ratio of the fragrance to glyceryl ricinoleate is from 1:1 to 28:1.

2. The liquid fragrance composition of claim 1, further comprising 0.3 wt % to 2 wt % of a thickening agent.

3. The liquid fragrance composition of claim 2, wherein the thickening agent is an acrylate/$C_{10-30}$ alkyl acrylate crosspolymer and/or xanthan gum.

4. The liquid fragrance composition of claim 1, wherein the liquid fragrance composition has a viscosity of 400 cP to 3000 cP.

5. The liquid fragrance composition of claim 1, wherein the liquid fragrance composition has a pH of 3.5 to 8.

6. The liquid fragrance composition of claim 1, wherein the fragrance is present at a level of 10 wt % to 30 wt %, and the glyceryl ricinoleate is present at a level of 0.5 wt % to 2.5 wt %.

7. The liquid fragrance composition of claim 1, wherein the weight ratio of the fragrance to glyceryl ricinoleate is from 5:1 to 20:1.

8. The liquid fragrance composition of claim 1, wherein the fragrance contains the following components: (i) 0 wt % to 10 wt % of one or more Type (I) fragrance ingredients having a ClogP of less than 2, (ii) 80 wt % to 100 wt % of one or more Type (II) fragrance ingredients having a ClogP of 2 to 5, and (iii) 0 wt % to 20 wt % of one or more Type (III) fragrance ingredients having a ClogP of greater than 5.

9. The liquid fragrance composition of claim 1, wherein the fragrance contains 10 wt % or less of one or more Type (IV) fragrance ingredients having a primary hydroxyl group.

10. The liquid fragrance composition of claim 1, wherein the liquid fragrance composition is an oil-in-water emulsion, in which a plurality of fragrance oil droplets is dispersed in water, and the fragrance oil droplets each have a particle size of 0.1 μm to 200 μm in diameter.

11. The liquid fragrance composition of claim 1, further comprising a plurality of microcapsules, wherein each of the microcapsules contains a microcapsule core and a microcapsule wall encapsulating the microcapsule core.

12. A consumer product comprising a liquid fragrance composition of claim 1.

13. The consumer product of claim 12, wherein the consumer product is an air freshener, an air spray, a concentrated floor cleaner, or a laundry scent booster.

14. The consumer product of claim 12, wherein the consumer product is a shampoo, a hair conditioner, a body lotion, a fine fragrance, or a hand soap.

15. The liquid fragrance composition of claim 1, wherein the glyceryl ricinoleate is present at a level of 0.5 wt % to 2.5 wt %.

16. The liquid fragrance composition of claim 1, wherein the fragrance is present at a level of 3 wt % to 30 wt %.

17. The liquid fragrance composition of claim 11, wherein the microcapsule wall comprises a biopolymer.

* * * * *